United States Patent
Zeltwanger et al.

(10) Patent No.: US 10,441,402 B2
(45) Date of Patent: Oct. 15, 2019

(54) INCONTINENCE DEVICE

(71) Applicant: Rinovum Subsidiary 2, LLC, Monroeville, PA (US)

(72) Inventors: Andrew P. Zeltwanger, Leechburg, PA (US); Camaria Lehman, Harmony, PA (US)

(73) Assignee: RINOVUM SUBSIDIARY 2, LLC, Monroeville, PA (US)

( * ) Notice: Subject to any disclaimer, the term of this patent is extended or adjusted under 35 U.S.C. 154(b) by 149 days.

(21) Appl. No.: 15/657,581

(22) Filed: Jul. 24, 2017

(65) Prior Publication Data

US 2018/0021121 A1  Jan. 25, 2018

Related U.S. Application Data

(60) Provisional application No. 62/366,471, filed on Jul. 25, 2016.

(51) Int. Cl.
*A61F 2/00* (2006.01)

(52) U.S. Cl.
CPC ............ *A61F 2/005* (2013.01); *A61F 2/0036* (2013.01); *A61F 2220/0091* (2013.01); *A61F 2230/0065* (2013.01); *A61F 2250/0012* (2013.01); *A61F 2250/0078* (2013.01)

(58) Field of Classification Search
CPC ................... A61F 2/0036; A61F 2/005; A61F 2230/0065; A61F 2250/0078; A61F 2220/0091; A61F 2250/0012
USPC .......................... 600/29–32, 37; 128/834–841
See application file for complete search history.

(56) References Cited

U.S. PATENT DOCUMENTS

| | | | |
|---|---|---|---|
| 3,196,873 A | 7/1965 | Bletzinger et al. | |
| 4,536,178 A | 8/1985 | Lichstein et al. | |
| 4,726,805 A | 2/1988 | Sanders, III | |
| 4,846,819 A | 7/1989 | Welch | |
| 5,007,894 A * | 4/1991 | Enhorning | A61F 2/005 |
| | | | 128/DIG. 25 |
| 5,036,867 A | 8/1991 | Biswas | |
| 5,256,133 A | 10/1993 | Spitz | |
| 5,386,836 A * | 2/1995 | Biswas | A61F 2/005 |
| | | | 128/885 |
| 5,437,628 A | 8/1995 | Fox et al. | |
| 5,671,755 A | 9/1997 | Simon et al. | |
| 5,771,899 A | 6/1998 | Martelly et al. | |
| 5,785,640 A | 7/1998 | Kresch et al. | |
| 6,090,098 A | 7/2000 | Zunker et al. | |
| 6,142,928 A | 11/2000 | Zunker et al. | |

(Continued)

*Primary Examiner* — Navin Natnithithadha
*Assistant Examiner* — Sunita Reddy
(74) *Attorney, Agent, or Firm* — Welsh Flaxman & Gitler LLC

(57) ABSTRACT

An incontinence device is used to apply supporting pressure to an anterior wall of an inferior third of a vaginal canal in the approximate plane of a pubococcygeal muscle and ultimately to a urethra for controlling incontinence. The incontinence device includes a first member having a first end and second end, as well as a second member resiliently connected to the first member. The second member is biased outwardly from the first member to direct the first end of the first member toward the anterior wall of the vaginal canal in a manner providing a support structure transferring upward force for support of the urethra by the first end of the first member.

20 Claims, 4 Drawing Sheets

(56) References Cited

U.S. PATENT DOCUMENTS

| | | | |
|---|---|---|---|
| 6,158,435 A * | 12/2000 | Dorsey | A61F 2/005 128/830 |
| 6,413,206 B2 | 7/2002 | Biswas | |
| 6,418,930 B1 | 7/2002 | Fowler | |
| 6,460,542 B1 | 10/2002 | James | |
| 6,503,190 B1 * | 1/2003 | Ulmsten | A61F 2/005 128/834 |
| 6,645,136 B1 | 11/2003 | Zunker et al. | |
| 6,645,137 B2 | 11/2003 | Ulmsten et al. | |
| 6,652,477 B2 | 11/2003 | Karapasha et al. | |
| 6,676,594 B1 | 1/2004 | Zunker et al. | |
| 6,695,763 B2 | 2/2004 | Zunker et al. | |
| 6,808,485 B2 | 10/2004 | Zunker | |
| 6,939,289 B2 | 9/2005 | Zunker et al. | |
| 7,263,999 B2 | 9/2007 | Kaseki et al. | |
| 7,351,195 B2 | 4/2008 | Farrell | |
| 7,628,156 B2 | 12/2009 | Astani et al. | |
| 7,717,892 B2 | 5/2010 | Bartning et al. | |
| 7,736,298 B2 | 6/2010 | Guerquin et al. | |
| 7,771,344 B2 | 8/2010 | Ziv | |
| 7,892,163 B2 | 2/2011 | Bartning et al. | |
| 7,935,098 B2 | 5/2011 | Bartning et al. | |
| 7,942,806 B2 | 5/2011 | Tracey et al. | |
| 7,981,021 B2 | 7/2011 | Spitz et al. | |
| 7,981,024 B2 | 7/2011 | Levy | |
| 8,047,980 B2 | 11/2011 | Bartning et al. | |
| 8,127,768 B2 | 3/2012 | Ziv | |
| 8,177,706 B2 | 5/2012 | Bartning et al. | |
| 8,221,374 B2 | 7/2012 | Hou et al. | |
| 8,302,608 B2 | 11/2012 | Harmanli | |
| 8,323,176 B2 | 12/2012 | Spitz et al. | |
| 8,435,168 B2 | 5/2013 | Ziv et al. | |
| 8,608,639 B2 | 12/2013 | Bartning et al. | |
| 8,613,698 B2 | 12/2013 | Bartning et al. | |
| 8,617,047 B2 | 12/2013 | Sinai et al. | |
| 8,651,109 B2 | 2/2014 | Ziv et al. | |
| 8,652,026 B2 | 2/2014 | Zunker et al. | |
| 8,652,027 B2 | 2/2014 | Hou et al. | |
| 8,753,258 B2 | 6/2014 | Bartning et al. | |
| 8,911,344 B2 | 12/2014 | Altan et al. | |
| 8,911,345 B2 | 12/2014 | Ziv et al. | |
| 8,920,302 B2 | 12/2014 | Levy | |
| 8,923,493 B2 | 12/2014 | Hillis et al. | |
| 9,022,919 B2 | 5/2015 | Ellefson et al. | |
| 9,050,183 B2 | 6/2015 | Bartning et al. | |
| 9,078,726 B2 | 7/2015 | Karapasha | |
| 9,173,768 B2 | 11/2015 | Bartning et al. | |
| 9,198,748 B2 | 12/2015 | Ziv et al. | |
| 9,320,640 B2 | 4/2016 | Durling et al. | |
| 9,339,361 B2 | 5/2016 | Ziv et al. | |
| 9,339,363 B2 | 5/2016 | Ziv et al. | |
| 9,339,364 B2 | 5/2016 | Durling et al. | |
| 9,393,090 B2 | 7/2016 | Karapasha | |
| 9,398,984 B2 | 7/2016 | Hou et al. | |
| 9,408,685 B2 | 8/2016 | Hou et al. | |
| 9,439,748 B2 | 9/2016 | Durling et al. | |
| 9,549,798 B2 | 1/2017 | Sinai et al. | |
| 9,597,222 B2 | 3/2017 | Durling et al. | |
| 9,655,769 B2 | 5/2017 | Ziv et al. | |
| 2002/0083949 A1 | 7/2002 | James | |
| 2004/0084054 A1 * | 5/2004 | Kaseki | A61F 6/08 128/885 |
| 2004/0249238 A1 * | 12/2004 | Farrell | A61F 2/005 600/29 |
| 2005/0016545 A1 * | 1/2005 | Nissenkorn | A61F 2/005 128/834 |
| 2005/0113228 A1 | 5/2005 | Marcotte | |
| 2008/0033230 A1 | 2/2008 | Bartning et al. | |
| 2008/0228027 A1 * | 9/2008 | Guerquin | A61F 2/005 600/30 |
| 2008/0281149 A1 | 11/2008 | Sinai et al. | |
| 2009/0318750 A1 | 12/2009 | Ziv et al. | |
| 2012/0071709 A1 * | 3/2012 | Spitz | A61F 2/005 600/30 |
| 2012/0136199 A1 | 5/2012 | Hou et al. | |
| 2012/0165599 A1 * | 6/2012 | Ellefson | A61F 13/26 600/29 |
| 2012/0259162 A1 | 10/2012 | Karapasha | |
| 2012/0259166 A1 | 10/2012 | Karapasha | |
| 2012/0259167 A1 | 10/2012 | Karapasha et al. | |
| 2012/0271098 A1 | 10/2012 | Ziv et al. | |
| 2013/0012764 A1 * | 1/2013 | Herbowy | A61F 2/0009 600/29 |
| 2013/0160272 A1 * | 6/2013 | Bartning | A61F 2/005 29/428 |
| 2013/0192606 A1 | 8/2013 | Ziv et al. | |
| 2014/0100416 A1 * | 4/2014 | Durling | A61F 2/005 600/29 |
| 2014/0275744 A1 * | 9/2014 | Rosen | A61F 2/0031 600/29 |
| 2015/0297392 A1 | 10/2015 | Karapasha | |
| 2015/0305844 A1 | 10/2015 | Schuman et al. | |
| 2016/0015500 A1 | 1/2016 | Ziv et al. | |
| 2016/0016040 A1 * | 1/2016 | Horsley | A63B 23/20 482/121 |
| 2016/0220342 A1 | 8/2016 | Ziv et al. | |
| 2016/0235583 A1 | 8/2016 | Durling et al. | |
| 2016/0296379 A1 | 10/2016 | Brown et al. | |
| 2016/0296380 A1 | 10/2016 | Graham et al. | |
| 2016/0374788 A1 | 12/2016 | Ramachandra et al. | |
| 2017/0014217 A1 | 1/2017 | Patrusky | |
| 2017/0100278 A1 | 4/2017 | Ziv et al. | |

* cited by examiner

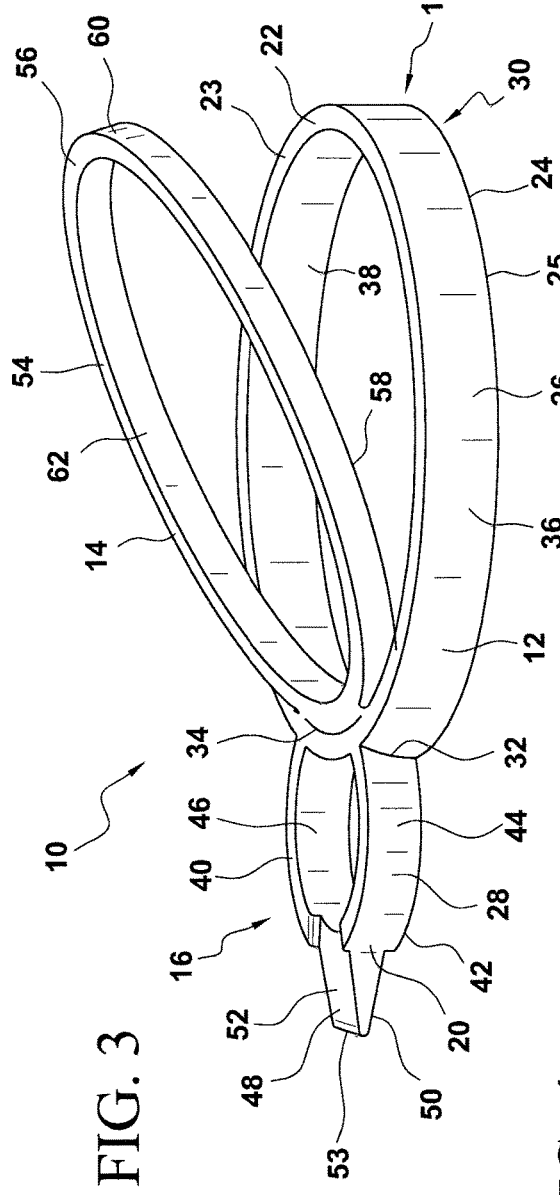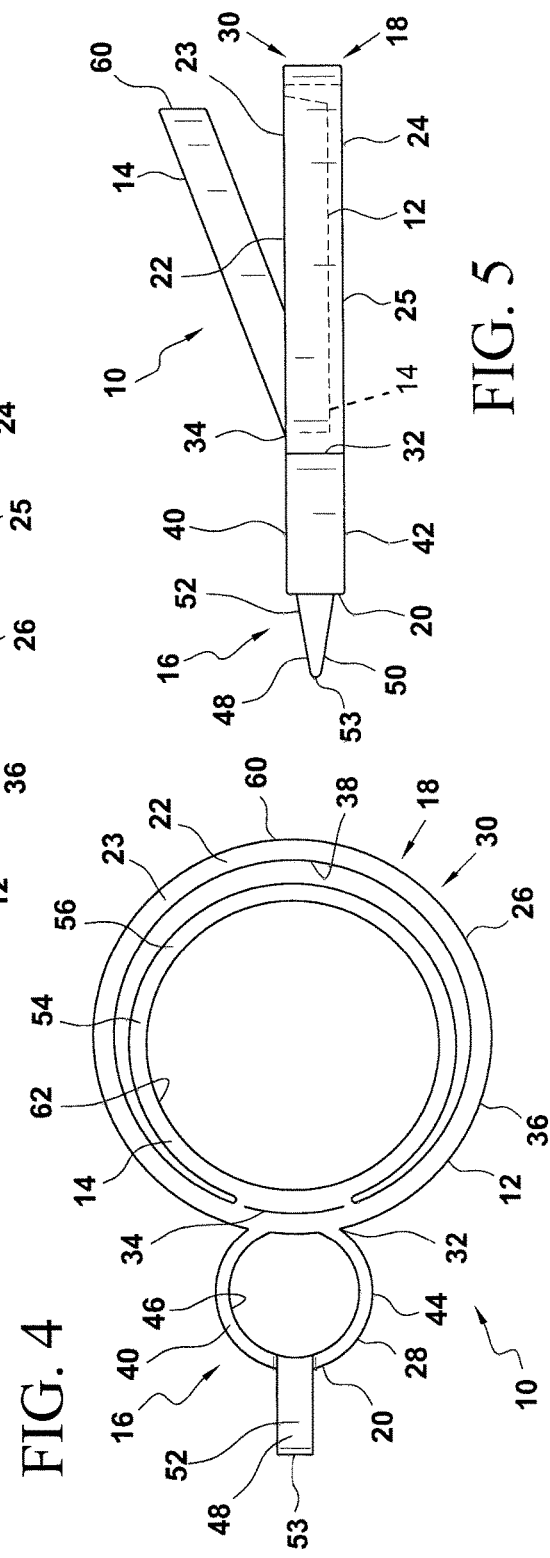

INCONTINENCE DEVICE

CROSS REFERENCE TO RELATED APPLICATION

This application claims the benefit of U.S. Patent Application Ser. No. 62/366,471, entitled "STRESS INCONTINENCE DEVICE," filed Jul. 25, 2016.

BACKGROUND OF THE INVENTION

1. Field of the Invention

The present invention generally relates to an incontinence device.

2. Description of the Related Art

By way of background, it is well appreciated the female pelvic region includes portions of the female reproductive system, female gastrointestinal system and the female urinary system. The female pelvic region is shown in FIGS. 1 and 2, and includes a vagina 200, a cervix 210, a uterus 212, a urethra 208, a bladder 214 and a symphysis pubis 216. The vagina 200 includes an introital opening 218 that exits the human body and contains a vaginal canal 202 extending from the introital opening 218 to the cervix 210. The vaginal canal 202 has a length that ranges from between about 4 to about 6 inches in most women. The cervix 210 is the entrance to the uterus and is located between the upper aspect of the vaginal canal 202 and the uterus 212. The vaginal canal 202 has an inner periphery 220.

The inner periphery 220 of the vaginal canal is composed of a right lateral wall 222, a left lateral wall (not shown), an anterior wall 206, and a posterior wall 204. The four walls encompass the entire 360 degrees of the inner periphery 220. The anterior wall 206 is located closest to the urethra 208 and the urethra 208 is located between the symphysis pubis 216 and the vagina 200.

The vaginal canal 202 is commonly divided into three approximately equal sections, that is, the inferior third 236, the middle third 237 and the superior third 238, each representing about one-third of the overall length. Each section is approximately 2 inches in length. The inferior third 236 of the vaginal canal 202 is the most important section for alleviating female urinary incontinence because of its proximity to the urethra 208. The inferior third 236 of the vaginal canal 202 is the location affected by placement of vaginal insert devices which alleviate conditions of female incontinence, regardless of where in the vagina 202 the bulk of the device rests after insertion. In the erect female, the middle third 237 of the vaginal canal 202 is horizontally offset from the inferior third 236 of the vaginal canal 202 which is substantially parallel to the urethra 208. The urethra 208 is situated between the inferior third 236 of the vaginal canal 202 and the symphysis pubis 216, which is a bony structure situated adjacent to a front portion of the human torso and may be referred to as the bladder neck region.

The urethra 208, also referred to as a urethral tube, is a hollow tubular structure positioned anterior to the vaginal canal 202. The urethra 208 extends from a first opening 226 that exits the human body to a second opening 228 situated at the lower surface of the bladder 214. The posterior urethrovesical angle is formed where the urethra 208 enters the bladder 214. The urethra 208 has a length of about 1.5 inches in most women. The urethra 208 functions to discharge urine, which is temporarily stored in the bladder 214, from the human body. The urethra 208 has a plurality of urethral sphincter muscles 232 located along the length of its inner periphery. The urethral sphincter muscles 232 are situated below the opening 228 and are ring like muscles that normally maintain constriction of the urethra 208 to prevent the passage of urine. The relaxation of the urethral sphincter muscles 232 by normal physiological functioning will permit urine to be voluntarily expelled from the body.

The pubococcygeal muscle 233 originates at the symphysis pubis 216 and extends to the inferior extent of the coccyx 234 with a passage in the center of the muscle through which the rectum 235, vagina 200 and urethra 208 pass. The posterior portion of the passage through the pubococcygeal muscle 233 normally provides support to the posterior portion of the urethra 208 through the soft tissues of the rectum 235 and vagina 200 which assist in maintaining constriction of the urethra 208 to prevent the passage of urine. When the pubococcygeal muscle 233 stretches due to childbirth or generally relaxes due to the normal aging process, support to the posterior portion of the urethra 208 is reduced and unintentional flow of urine through the urethra 208 may occur, particularly when pressure is applied to the bladder 214 during a cough or other abdominal contraction. This condition is known as stress incontinence. Replacing or supplementing support to the posterior side of the urethra 208 can help to prevent the unintentional flow of urine through the urethra 208.

SUMMARY OF THE INVENTION

It is, therefore, an object of the present invention to provide an incontinence device used to apply supporting pressure to an anterior wall of an inferior third of a vaginal canal in the approximate plane of a pubococcygeal muscle and ultimately to a urethra for controlling incontinence. The incontinence device includes a first member having a first end and second end, as well as a second member resiliently connected to the first member. The second member is biased outwardly from the first member to direct the first end of the first member toward the anterior wall of the vaginal canal in a manner providing a support structure transferring upward force for support of the urethra by the first end of the first member.

It is also an object of the present invention to provide an incontinence device wherein the incontinence device is constructed of a flexible, biocompatible polymeric or elastomeric material.

It is another object of the present invention to provide an incontinence device wherein the first member is shaped and dimensioned for positioning upon either a posterior wall or an anterior wall of the vaginal canal.

It is a further object of the present invention to provide an incontinence device wherein the first member is substantially flat along its upper and lower surfaces such that the upper surface lies in a first plane and the lower surface lies in a second plane that is substantially parallel to the first plane.

It is also an object of the present invention to provide an incontinence device wherein the first member includes a first ring element at the first end of the first member and a second ring element at the second end of the first member, wherein the first ring element and the second ring element share a segment at a junction of the first ring element and the second ring element.

It is another object of the present invention to provide an incontinence device wherein the second member is constructed as a ring.

It is a further object of the present invention to provide an incontinence device wherein the second member has a diameter that is slightly smaller than that of the first ring element such that the second member fits within the first ring element of the first member when the incontinence device is compressed to a low profile deployment configuration.

It is also an object of the present invention to provide an incontinence device wherein the second member is secured to the first member at the junction of the first and second ring elements of the first member in a manner allowing the second member to pivot relative to the first member.

It is another object of the present invention to provide an incontinence device wherein the first ring element is larger than the second ring element.

It is a further object of the present invention to provide an incontinence device wherein the second ring element of the first member is provided with a pressure application member at a position diametrically opposed to the junction of the first and the second ring elements of the first member, wherein the pressure application member is shaped and dimensioned to provide support to the urethra at the first end of the first member.

It is also an object of the present invention to provide an incontinence device wherein the pressure application member includes a wedge configuration with a bottom surface extending at an angle from a lower surface of the second ring element of the first member and a top surface extending at an angle from an upper surface of the second ring element of the first member to a tip of the wedge.

It is another object of the present invention to provide an incontinence device wherein a pressure application member is provided at the first end of the first member, the pressure application member being shaped and dimensioned to provide support to the urethra at the first end of the first member.

It is a further object of the present invention to provide an incontinence device wherein the pressure application member is symmetrical allowing for either side thereof to provide support to the urethra.

It is also an object of the present invention to provide an incontinence device including a removal string attached to the incontinence device first member.

It is also an object of the present invention to provide an incontinence device wherein the removal string is attached to the first member.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 3 is a perspective view of the incontinence device.

FIG. 4 is a top plan view of the incontinence device shown in FIG. 3.

FIG. 5 is a side elevation view of the incontinence device shown in FIG. 3, which shows in broken lines the second member ring recessed within the first ring member.

DESCRIPTION OF THE PREFERRED EMBODIMENT

Figure 1:
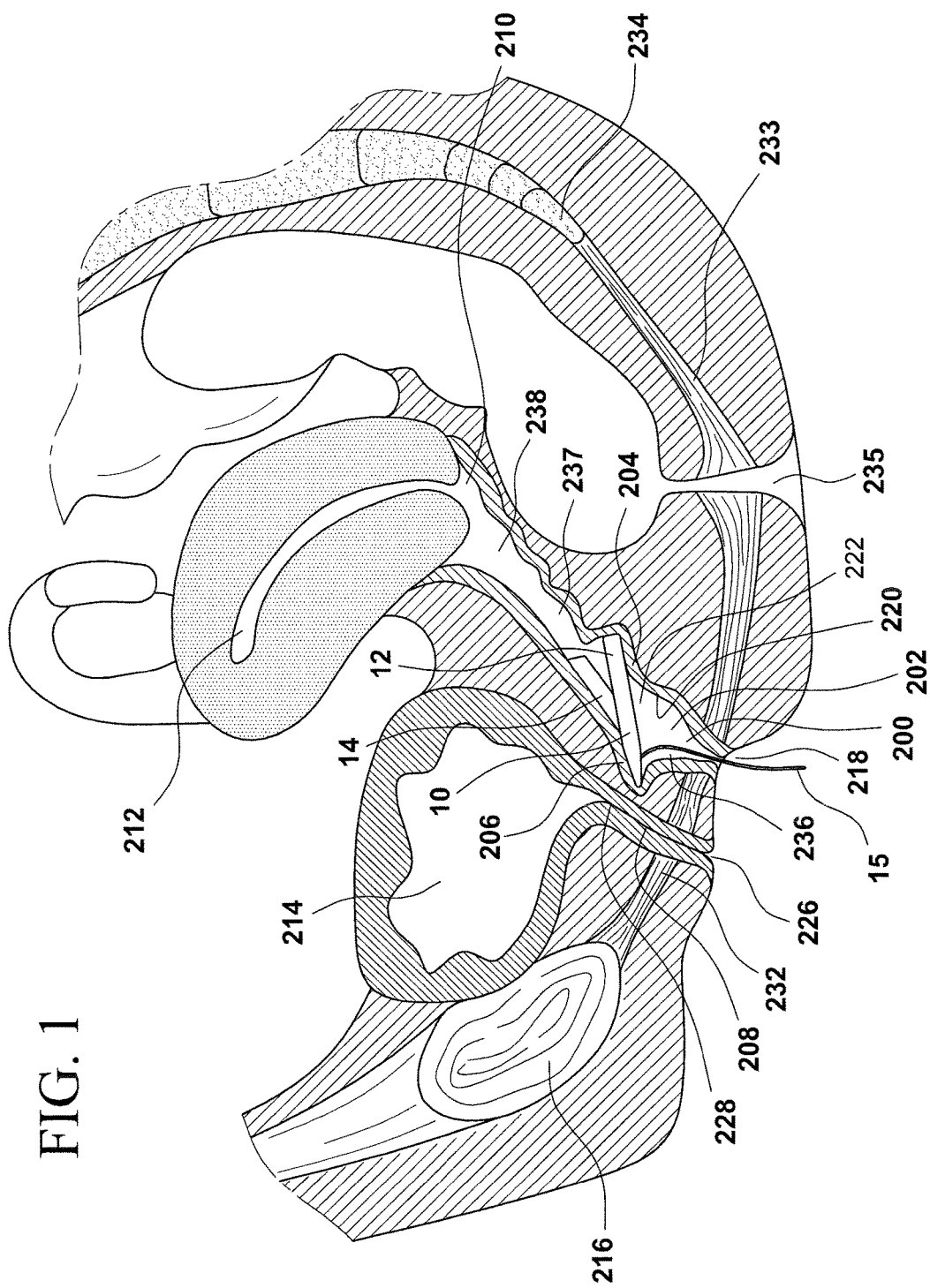
FIG. 1 a cross section view of the female pelvic region with the present incontinence device inserted with the lower surface of the large first ring element facing the posterior wall of the vaginal canal.

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

Referring to FIGS. 1 to 5, and considering the female pelvic anatomy as described above with reference to FIGS. 1 and 2, the present stress incontinence device 10 is adapted for positioning such that the first end 16 rests in the plane of pubococcygeal muscle 233 with the remainder of the stress incontinence device 10 in central and superior portions of vaginal canal 202. The stress incontinence device 10 is positioned such that the pressure application member 48 at the first end 16 of the stress incontinence device can be used to apply pressure support to the anterior wall 206 of the inferior third 236 of the vaginal canal 202 in the approximate plane of the pubococcygeal muscle 233 and ultimately to the urethra 208 for controlling incontinence. As will be discussed below in greater detail, the incontinence device 10 may be positioned within the vaginal canal with either the large first ring element 26 of the first member 12 supported upon the posterior wall 204 of the vaginal canal 202 or the large first ring element 26 of the first member supported upon the anterior wall 206 of the vaginal canal 202; as such, the stress incontinence device 10 may be insert upside down.

The incontinence device 10 is constructed of a material that is flexible in nature, such as a heavy silicone, so that the stress incontinence device 10 can collapse inside an applicator. It is further contemplated the stress incontinence device 10 may be composed of other flexible, biocompatible polymeric or elastomeric materials such as polyolefins, acetel, urethane, ABS, or various thermoplastic elastomers.

The stress incontinence device 10 includes a first member 12 and a second member 14 resiliently connected in a manner providing a support structure transferring upward force for support of the urethra 208 by the first end 20 of the first member 12. The stress incontinence device 10 includes a first end 16 and a second end 18. As will be appreciated based upon the following disclosure, the first member 12 of the stress incontinence device 10 is shaped and dimensioned for positioning upon either the posterior wall 204 or the anterior wall 206 of the vaginal canal 202, while the second member 14 is biased outwardly from the first member 12 in a manner causing contact with the opposite wall of the vaginal canal 202 to direct the first end 16 of the stress incontinence device 10, in particular, the first end 20 of the first member 12 toward the anterior wall 206 of the vaginal canal 202 and ultimately into contact with the urethra 208 for controlling incontinence.

The first member 12 is substantially flat along its upper and lower surfaces 22, 24 such that the upper surface 22 lies in a first plane and the lower surface 24 lies in a second plane that is substantially parallel to the first plane. With this in mind, it is appreciated the lower surfaces 25, 42 of the first and second ring elements 26, 28 are slightly offset such that the lower surface 42 of the small second ring element 28 sits slightly above the lower surface 25 of the large first ring element 26. It is appreciated relative terms such as upper, lower, top and bottom are used throughout the present disclosure, and these terms are merely used in reference to the various drawings employed in disclosing the present invention.

The first member 12 is composed of a large first ring element 26 and a small second ring element 28. The first and second ring elements 26, 28 used in the construction of the stress incontinence device 10 are shaped and dimensioned to optimize support of the first member 12, in particular, support of the large first ring element 26, along the posterior wall 204 or anterior wall 206 of the vaginal canal 202 in a manner allowing the small second ring element 28 at the first end 20 of the first member 12 to engage, and apply force to, the anterior wall 206 of the vaginal canal 202 for controlling incontinence.

With this in mind, the first member 12 includes a first end 20 at which the small second ring element 28 is positioned and a second end 30 at which the large first ring element 26 is positioned. The small second ring element 28 and the large first ring element 26 are joined at a junction 32 where the large first ring element 26 continues its circumference and the small second ring element 28 includes a small inward section, that is, the small second ring element 28 and the large first ring element 26 share an arcuate segment 34 at the junction 32, wherein the arcuate segment 34 is continuous with the large first ring element 26.

The large first ring element 26 includes an upper surface 22, a lower surface 24, an outer side wall 36 between the upper and lower surfaces 23, 25, and an inner side wall 38 between the upper and lower surfaces 23, 25. Similarly, the small second ring element 28 includes an upper surface 40, a lower surface 42, an outer side wall 44 between the upper and lower surfaces 40, 42, and an inner side wall 46 between the upper and lower surfaces 40, 42.

The small second ring element 28 is further provided with a pressure application member 48 at a position diametrically opposed to the junction 32 of the small second ring element 28 and the large first ring element 26. The pressure application member 48 is shaped and dimensioned to provide support to the urethra 208 at the first end 16 of the stress incontinence device 10. As such, the pressure application member 48 includes a wedge configuration with a bottom surface 50 extending at an angle from the lower surface 42 of the small second ring element 28 and a top surface 52 extending at an angle from the upper surface 40 of the small second ring element 28 to the tip 53 of the wedge to form an isosceles triangular configuration. While a wedge shape is disclosed above for the pressure application member it is contemplated the pressure application member could be more bulbous and/or rounded. In addition to the application of pressure, the small second ring element 28 acts as a secondary manual loop for removal, should string removal fail.

Figure 2:
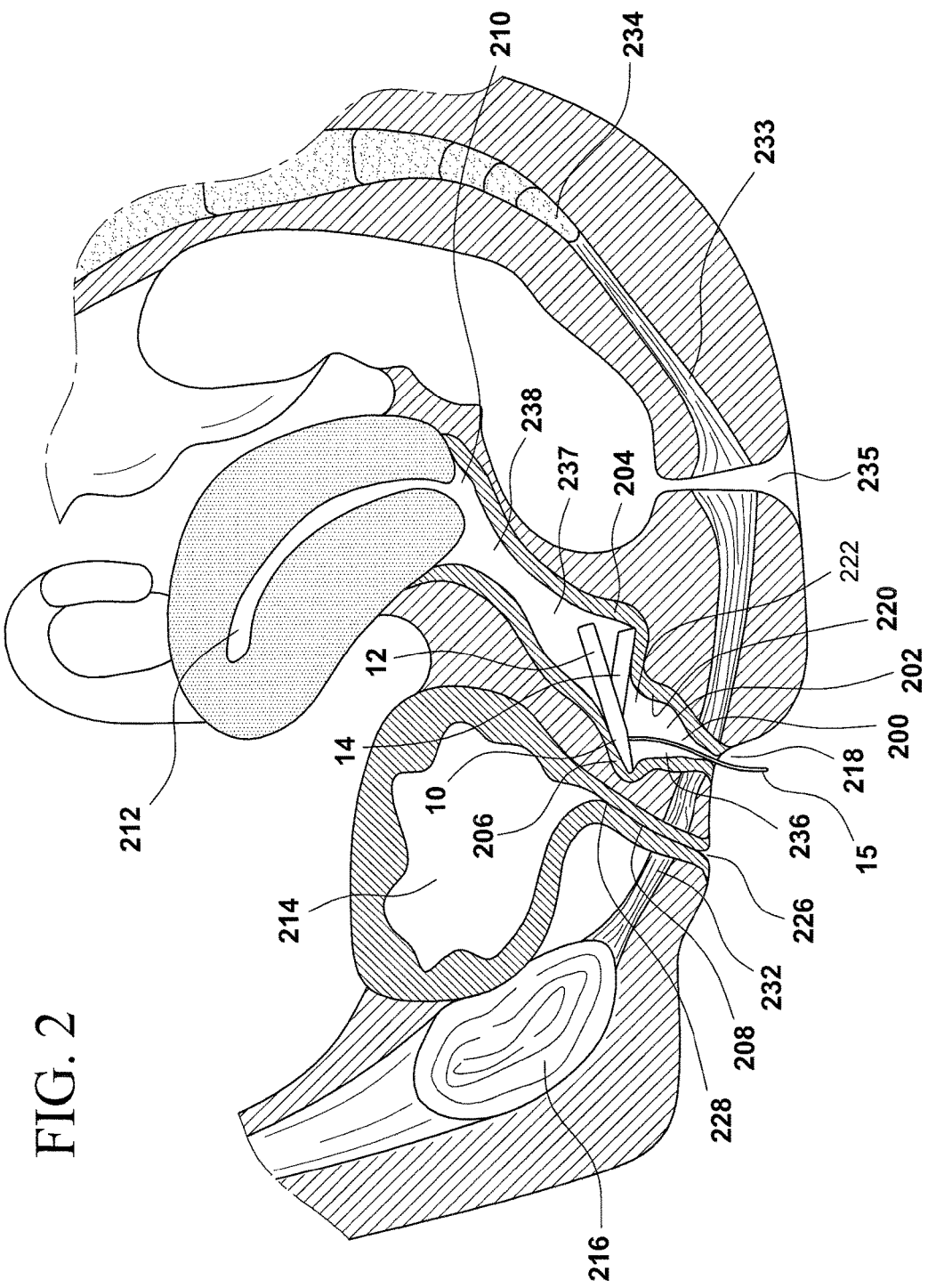
FIG. 2 a cross section view of the female pelvic region with the present incontinence device inserted with the lower surface of the first member facing the anterior wall of the vaginal canal.

The pressure application member 48, in particular, the bottom and top surfaces 50, 52 are angled so that the flat of the "blade" defined by the pressure application member provides the support to the urethra 208 (that is, the top surface 52 of the pressure application member 48 when the large first ring element 26 is supported upon the posterior wall 204 of the vaginal canal 202 or the bottom surface 50 of the pressure application member 48 when the large first ring element 26 is supported upon the anterior wall 206 of the vaginal canal 202) as the pressure application member 48 is brought into contact with the anterior wall 206 of the vaginal canal 202 and applies pressure to the urethra 202 (see FIGS. 1 and 2). As such, the pressure application member 48 is substantially symmetrical. In particular, the top surface 52 comes into contact with the anterior wall 206 of the vaginal canal 202 to provide support to the urethra 208 when the large first ring element 26 is supported upon the posterior wall 204 of the vaginal canal 202, and the bottom surface 50 of the pressure application member 48 comes into contact with the anterior wall 206 of the vaginal canal 202 to provide support to the urethra 208 when the large first ring element 26 is supported upon the anterior wall 206 of the vaginal canal 202 (see FIGS. 1 and 2).

Figure 6:
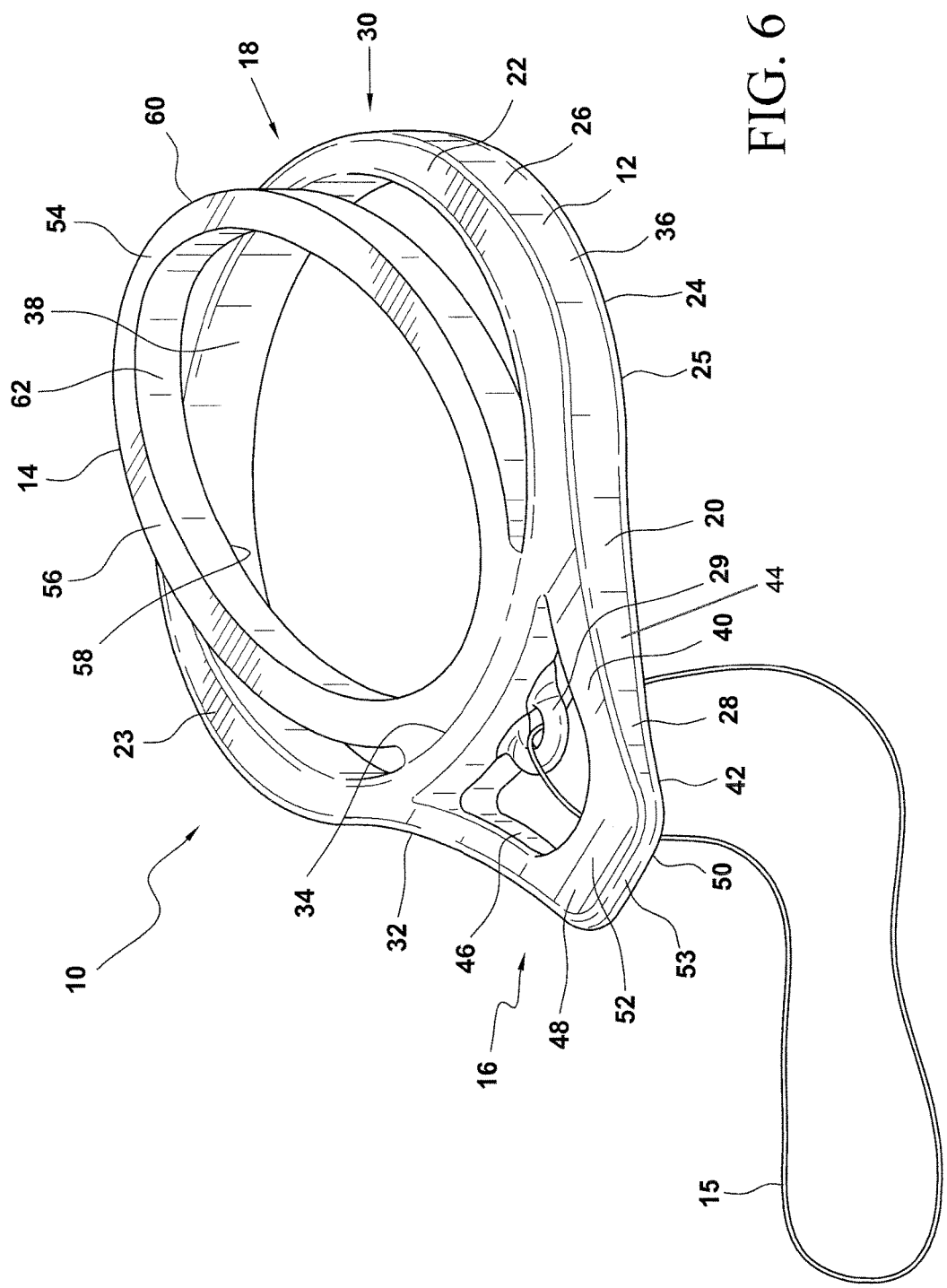
FIG. 6 is a perspective view of an alternative embodiment of an incontinence device.

In accordance with an alternate embodiment shown in FIG. 6, the small second ring element 28 takes a shape that is not completely circular, but rather includes an arcuate front end adjacent to the pressure application member and straightening side walls that are ultimately coupled with the large first ring element at the junction in a manner similar to the embodiment disclosed above. With this in mind, and in accordance with this embodiment, the small second ring element includes an upper surface 40, a lower surface 42, an outer side wall 44 between the upper and lower surfaces 40, 42, and an inner side wall 46 between the upper and lower surfaces 40, 42. The small second ring element 28 is further provided with a pressure application member 48 at a position diametrically opposed to the junction 32 of the small second ring element 28 and the large first ring element 26.

As with the prior embodiment, the pressure application member 48 is shaped and dimensioned to provide support to the urethra 208 at the first end 16 of the stress incontinence device 10. The pressure application member 48 includes a wedge configuration with a bottom surface 50 extending at an angle from the lower surface 42 of the small second ring element 28 and a top surface 52 extending at an angle from the upper surface 40 of the small second ring element 28 to the tip 53 of the wedge to form an isosceles triangular configuration. In contrast to the embodiment disclosed with reference to FIGS. 1 to 5, the pressure application member 48 of the this embodiment is integrated with the remainder of the small second ring element 28 such that there is no distinct transition. Rather, the small second ring element 28 includes a smooth exterior surface. While a wedge shape is disclosed above for the pressure application member it is contemplated the pressure application member could be more bulbous and/or rounded.

A string removal loop 29 is also provided within the small second ring element 28. The sting removal loop 29 is shaped and dimensioned for attachment of the removal string 15 thereto and is formed along the junction so as to extend into the interior space defined by the small second ring element 28. In addition to the application of pressure, the small second ring element 28 acts as a secondary manual loop for removal, should removal string 15 fail.

As with the embodiment disclosed above with reference to FIGS. 3 to 5, the pressure application member 48, in particular, the bottom and top surfaces 50, 52 are angled so that the flat of the "blade" defined by the pressure application member provides the support to the urethra 208 as the pressure application member 48 is brought into contact with the anterior wall 206 of the vaginal canal 202 and applies pressure to the urethra 202.

The second member 14 is also constructed as a ring. As with the first and second ring elements 26, 28, the second member ring 54 includes an upper surface 56, a lower surface 58, an outer side wall 60 between the upper and lower surfaces 56, 58, and an inner side wall 62 between the upper and lower surfaces 56, 58. The second member ring 54 has a diameter that is slightly smaller than that of the large first ring element 26 such that the second member ring 54 fits within the large first ring element 26 when the stress incontinence device 10 is compressed to its low profile deployment configuration. The second member ring 54 is secured to the first member 12 at the junction 32 of the first and second ring elements 26, 28 in a manner allowing the second member ring 54 to pivot relative to the first member 12. The second member ring 54 is aligned to pivot relative to the large first ring element 26 of the first member 12 such that the second member ring 54 pivots about an axis that extends transvers to the arcuate segment 34 at the junction 32 of the large first ring element 26 and the small second ring element 28. With this arrangement, and if one where to pivot the second member ring 54 about the axis it would fit within the large first ring element 26. This ability to recess the second member ring 54 within the first ring element 26 provides for a substantial profile reduction and thereby assists in deployment and removal. It is appreciated that while the second member ring 54 is disclosed herein as being slightly smaller than the large first ring element 26, the sizes could be flipped without departing from the spirit of the present invention, that is, the first ring element 26 could be made to have a smaller diameter so that it fits within second member ring 54.

As mentioned above, the stress incontinence device 10 is constructed to allow for movement of the second member 14, that is, the second member ring 54, relative to the first member 12, that is, the large first ring element 26 and the small second ring element 28. The movement occurs as a result of a resilient bias created at the junction of the second member ring 54 and the second member 14 which biases the second member ring 54 in a direction away from the large first ring element 26. In accordance with a preferred embodiment, the positioning of the large first ring element 26 and the second member ring 54 in their fully expanded orientation is such that that they are set at a physiologically appropriate angle (34-44 degrees, depending on flexion capabilities). In particular, the bias causes the portion of the second member ring 54 diametrically opposed to the junction 64 of the second member ring 54 and the second member 14 to move away from the portion of the large first ring element 26 diametrically opposed to the junction 64 of the second member ring 54 and the second member 14 in a manner allowing the controlled expansion of the stress incontinence device 10 that forces the pressure application member 48 toward the anterior wall 206 of the vaginal canal 202 when the stress incontinence device 10 is properly positioned within the vaginal canal 202 to apply pressure to the anterior wall 206 of the vaginal canal 202 and ultimately to the urethra 208 for controlling incontinence.

In practice, the stress incontinence device 10 is prepackaged within an inserter for deployment within the vaginal canal 202. Although not shown it is contemplated an inserter would simply be a "tubular structure" in which the stress incontinence device 10 is drawn into a pre-collapsed orientation to ease initial placement into the vagina. It would then, however, need to be "pushed out" of the tube to remain in the vagina.

While in the inserter the second member 14 is collapsed into the first member 12 so as to reduce the profile of the stress incontinence device 10 and ease insertion within the vaginal canal (that is, the insertion state of the stress incontinence device 10). The stress incontinence device 10 is then inserted within the vaginal canal 202 and positioned with the lower surface of the first member 12 in contact with the posterior wall 204 of the vaginal canal 202. In particular, the stress incontinence device 10 is inserted into the vagina 200 with the large first ring element 26 and the second member ring 54 on the second end 18 of the stress incontinence device 10 entering the vagina 200 first. The small second ring element 28 and pressure application member 48 on the first end 16 of the stress incontinence device 10 enters the vagina 200 last. The large first ring element 26 and the second member ring 54, which compress during entry, into the vagina expand in the deep portion of the vagina 200 which, in the erect female, is above but generally parallel to the muscles in the pelvic floor. This maintains the device in the vagina 200.

The pressure application member 48 of the stress incontinence device 10 then rests in the deep portion of the vagina 200. The vagina 200 of the erect female bends inferiorly and in an anterior direction, passing through the muscles of the pelvic floor. The small second ring element 28 and pressure application member 48 on the first end 16 of the stress incontinence device 10 rest in this part of the vagina 200 such that the support feature falls in the plane of the pelvic floor muscles.

Once the stress incontinence device 10 is properly positioned within the vaginal canal 202, the second member 14 is released allowing the second member ring 54 to move outwardly away from the large first ring element 26. It is appreciated, the small second ring element 28 at the first end 16 of the stress incontinence device 10 flairs and provides positive positioning support around the opening in the pelvic floor opposite of the large first ring element 26 and the second member ring 54 to help secure the stress incontinence device 10 in place.

The movement of the second member ring 54 away from the large first ring element 26 causes the pressure application member 48 at the first end 20 of the first member 12 to move into contact with the anterior wall 206 of the vaginal canal 202 in a manner applying pressure thereto that ultimately applies pressure to the urethra 208 for controlling incontinence. Cooperation between a stress incontinence device 10 positioned in the vagina 200 and the symphysis pubis 216 allows the urethra 208 to be compressed upon itself thereby providing a means to alleviate involuntary urine flow from the bladder.

When deployed with the lower surface 25 of the large first ring element 26 supported upon the posterior wall 204 of the vaginal canal as shown in FIG. 1, the top surface 52 of the pressure application member 48 places a supporting force on the posterior wall 204 of the urethra 208 in a direction that is substantially perpendicular to the lumen of the urethra 208. This support emulates the natural support of the pelvic floor muscles which prevents unintended relief of the bladder through the urethra in normal, healthy physiological conditions.

In particular, the positioning of the large first ring element 26 and the second member ring 54 in their fully expanded orientation (that is, the deployed state of the stress incontinence device 10) is such that that they are set at a physiologically appropriate angle (34 -44 degrees, depending on flexion capabilities) to cause the desired interior with the anterior wall and the urethra 208. The large first ring element 26 and the second member ring 54, in conjunction with the opening in the pelvic floor, provide the support structure and transfer upward force for the urethral support to the first end 20 of the first member 12 at the first end 16 of the stress incontinence device 10. This interaction with the posterior wall 204 of the vaginal canal 202 creates the support base and force transfer for urethral support. The function of the stress incontinence device 10 is based on the concept that support of the pelvic floor muscles posterior to the urethra 208 in normal, healthy physiological conditions prevents unintended relief of the bladder through the urethra.

It is appreciated that it is not necessary to position the lower surface 24 of the first member 12 (in particular, the lower surface 25 of the large first ring 26) in contact with the posterior wall 204 of the vaginal canal 202, but the lower surface 24 of the first member 12 may be positioned in contact with the anterior wall 206 of the vaginal canal 202 as shown in FIG. 1. In such an arrangement, bottom surface 50 of the pressure application member 48 comes into contact with the anterior wall 206 of the vaginal canal 202 to provide support to the urethra 208 when the lower surfaces 25, 42 of both the large first ring 26 and the small second ring element 28 are also supported upon the anterior wall 206 of the vaginal canal 202.

In particular, and as with the previously described deployment orientation, the stress incontinence device 10 is inserted into the vagina 200 with the large first ring element 26 and the second member ring 54 on the second end 18 of the stress incontinence device 10 entering the vagina 200 first. The small second ring element 28 and pressure application member 48 on the first end 16 of the stress incontinence device 10 enters the vagina 200 last. The pressure application member 48 of the stress incontinence device 10 then rests in the deep portion of the vagina 200. In contrast to the embodiment disclosed with reference to FIG. 1, the lower surface 24 of the first member 12 (that is, the lower surfaces 25, 42 of both the large first ring element 26 and small second ring element 28) faces the anterior wall 206 of the vaginal canal 202.

Once the stress incontinence device 10 is properly positioned within the vaginal canal 202, the second member 14 is released allowing the second member ring 54 to move outwardly away from the large first ring element 26. It is appreciated, the small second ring element 28 at the first end 16 of the stress incontinence device 10 flairs and provides positive positioning support around the opening in the pelvic floor opposite of the large first ring element 26 and the second member ring 54 to help secure the stress incontinence device 10 in place. The second member ring 54 moves away from the large first ring element 26 until the top surface of the second ring member 54 comes into contact with the posterior wall 204 of the vaginal canal 202, which in turn causes the pressure application member 48 at the first end 20 of the first member 12 to move toward the anterior wall 206 of the vaginal canal 202 in a manner applying pressure thereto that ultimately applies pressure to the urethra 208 for controlling incontinence. Cooperation between a stress incontinence device 10 positioned in the vagina 200 and the symphysis pubis 216 allows the urethra 208 to be compressed upon itself thereby providing a means to alleviate involuntary urine flow from the bladder. The bottom surface 50 of the pressure application member 48 places a supporting force on the posterior side of the urethra 208 in a direction that is substantially perpendicular to the lumen of the urethra 208. This support emulates the natural support of the pelvic floor muscles which prevents unintended relief of the bladder through the urethra 208 in normal, healthy physiological conditions. The large first ring element 26 and the second member ring 54, in conjunction with the opening in the pelvic floor, provide the support structuring and transfer upward force for the urethral support to the first end 20 of the first member 12 at the first end 16 of the stress incontinence device 10. This interaction with the posterior wall 204 of the vaginal canal 202 creates the support base and force transfer for urethral support.

Ultimately, the function of the stress incontinence device 10 is based on the concept that support of the pelvic floor muscles posterior to the urethra 208 in normal, healthy physiological conditions prevents unintended relief of the bladder through the urethra.

When it is desired to remove the stress incontinence device 10, the human user may simply pull upon the removal string 15. Pulling upon the removal string 15 causes the stress incontinence device 10 to move toward the introital opening 218 and out of the vaginal canal 202. As a result of the shape of the vaginal canal 202 and the introital opening 218, the first and second members 12, 14 move toward each other, that is, the second member ring 54 moves toward the large first ring element 26 and ultimately resembles the insertion state discussed above as it is finally pulled through the introital opening 218 and out of the vagina 200.

While the preferred embodiments have been shown and described, it will be understood that there is no intent to limit the invention by such disclosure, but rather, it is intended to cover all modifications and alternate constructions falling within the spirit and scope of the invention.

The invention claimed is:

1. An incontinence device used to apply supporting pressure to an anterior wall of an inferior third of a vaginal canal and ultimately to a urethra for controlling incontinence, comprising:
   a first member having a first end and a second end;
   a second member resiliently connected to the first member, and the second member is biased outwardly from the first member to direct the first end of the first member toward the anterior wall of the vaginal canal in a manner providing a support structure configured to transfer upward force for support of the urethra by the first end of the first member; and
   wherein the first member includes a first ring element at the first end of the first member and a second ring element in the same plane as the first ring element at the second end of the first member, wherein the first ring element and the second ring element share a segment at a junction of the first ring element and the second ring element.

2. The incontinence device according to claim 1, wherein the first member is shaped and dimensioned for positioning upon either the posterior wall or the anterior wall of the vaginal canal and in either position functions to provide a support structure configured to transfer upward force for support of the urethra.

3. The incontinence device according to claim 1, wherein the first member is substantially flat along its upper and lower surfaces such that the upper surface lies in a first plane and the lower surface lies in a second plane that is substantially parallel to the first plane.

4. The incontinence device according to claim 1, wherein the second member is constructed as a ring.

5. The incontinence device according to claim 4, wherein the second member has a diameter that is slightly smaller than that of the first ring element such that the second member fits within the first ring element of the first member when the incontinence device is compressed to a low profile deployment configuration.

6. The incontinence device according to claim 5, wherein the second member is secured to the first member at the junction of the first and second ring elements of the first member in a manner allowing the second member to pivot relative to the first member.

7. The incontinence device according to claim 1, wherein the second member is secured to the first member at the junction of the first and second ring elements of the first member in a manner allowing the second member to pivot relative to the first member.

8. The incontinence device according to claim 1, wherein the first ring element is larger than the second ring element.

9. The incontinence device according to claim 1, wherein a pressure application member is provided at the first end of the first member, the pressure application member being shaped and dimensioned to provide support to the urethra at the first end of the first member.

10. The incontinence device according to claim 9, wherein the pressure application member is symmetrical allowing for either side thereof to provide support to the urethra.

11. An incontinence device used to apply supporting pressure to an anterior wall of an inferior third of a vaginal canal and ultimately to a urethra for controlling incontinence, comprising:
   a first member having a first end and a second end;
   a second member resiliently connected to the first member, and the second member is biased outwardly from the first member to direct the first end of the first member toward the anterior wall of the vaginal canal in a manner providing a support structure that is configured to transfer upward force for support of the urethra by the first end of the first member; wherein the first member includes a first ring element at the first end of the first member and a second ring element at the second end of the first member, wherein the first ring element and the second ring element share a segment at a junction of the first ring element and the second ring element; and
   wherein the second ring element of the first member is provided with a pressure application member at a position diametrically opposed to the junction of the first and the second ring elements of the first member, wherein the pressure application member is shaped and dimensioned to provide support to the urethra at the first end of the first member.

12. The incontinence device according to claim 11, wherein the incontinence device is constructed of a flexible, biocompatible polymeric or elastomeric material.

13. The incontinence device according to claim 11, wherein the pressure application member includes a wedge configuration with a bottom surface extending at an angle from a lower surface of the second ring element of the first member and a top surface extending at an angle from an upper surface of the second ring element of the first member to a tip of the wedge.

14. The incontinence device according to claim 11, further including a removal string attached to the incontinence device.

15. The incontinence device according to claim 11, wherein the second member is secured to the first member at the junction of the first and second ring elements of the first member in a manner allowing the second member to pivot relative to the first member.

16. The incontinence device according to claim 11, wherein the second member has a diameter that is slightly smaller than that of the first ring element such that the second member fits within the first ring element of the first member when the incontinence device is compressed to a low profile deployment configuration.

17. An incontinence device used to apply supporting pressure to an anterior wall of an inferior third of a vaginal canal and ultimately to a urethra for controlling incontinence, comprising:
   a first member having a first end and a second end, the first member including a first ring element at the first end of the first member and a second ring element at the second end of the first member;
   a second member resiliently connected to the first member, and the second member is biased outwardly from the first member to direct the first end of the first member toward the anterior wall of the vaginal canal in a manner providing a support structure that is configured to transfer upward force for support of the urethra by the first end of the first member;
   a pressure application member is provided at the first end of the first member, the pressure application member being shaped and dimensioned to provide support to the urethra at the first end of the first member; and
   wherein the pressure application member includes a wedge configuration with a bottom surface extending at an angle from a lower surface of the second ring element of the first member and a top surface extending at an angle from an upper surface of the second ring element of the first member to a tip of the wedge.

18. The incontinence device according to claim 1, further including a removal string attached to the incontinence device.

19. The incontinence device according to claim 17, wherein the second member is secured to the first member at the junction of the first and second ring elements of the first member in a manner allowing the second member to pivot relative to the first member.

20. The incontinence device according to claim 17, wherein the second member has a diameter that is slightly smaller than that of the first ring element such that the second member fits within the first ring element of the first member when the incontinence device is compressed to a low profile deployment configuration.

* * * * *